US00PP10253P

United States Patent [19]

Hrebeniuk

[11] Patent Number: Plant 10,253

[45] Date of Patent: Feb. 24, 1998

[54] POINSETTIA PLANT NAMED 'FESTIVAL RED'

[75] Inventor: Alexander Hrebeniuk, Sugar Run, Pa.

[73] Assignee: Oglevee, Ltd., Connellsville, Pa.

[21] Appl. No.: 627,059

[22] Filed: Apr. 3, 1996

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 8,773 6/1994 Fruehwirth ..... Plt./86.4
P.P. 9,058 2/1995 Fruehwirth ..... Plt./86.4

*Primary Examiner*—Howard J. Locker
*Attorney, Agent, or Firm*—Webb Ziesenheim Bruening Logsdon Orkin & Hanson, P.C.

[57] ABSTRACT

A poinsettia plant named 'Festival Red' particularly characterized by the combined characteristics of triple form, dark green leaves and intense rich red bracts. Plants are long lasting in shipment, greenhouse and home, and have upright and moderately compact growth habit with free branching.

1 Drawing Sheet

BACKGROUND OF THE NEW PLANT

The present invention comrpises a new and distinct cultivar of *Euphorbia pulcherrima* known by the varietal name "Festival Red".

The new cultivar is a product of a planned breeding program of seedlings in November of 1993 in Sugar Run, Pa. The new cultivar when discovered carried the test number H57 and was a cross between a male parent H38 and a female parent H515, neither parent being a commercial or patented variety. The new cultivar was first asexually reproduced by cuttings in June of 1994 in Sugar Run, Pa. and has been repeatedly asexually reproduced by cuttings at Sugar Run, Pa. and at Lompoc, Calif. Continued observations from the vegetative cuttings have confirmed that the distinguishing features of this new cultivar come true, remain stable and are retained through successive propagations.

The following traits are determined to be basic characteristics of this new cultivar which in combination distingish this poinsettia as new and distinct:

1. Very long post harvest quality, up to 5 months.
2. Bracts having strong stems.
3. Dark green foliage.
4. Early flowering.
5. Free branching.
6. Intense rich red color of bracts.
7. Fully developed intense yellow cyathia.

The rich red color and fully developed cyathia represent an improvement over the commercial variety Freedom. The new variety is shorter than Freedom which has a plant height of about 40–41 cm, has a greater plant spread than Freedom which has a spread of about 50–51.5 cm, is more branched and has shorter leaves than Freedom. The cyathia of the new variety are also larger than those of Freedom.

DESCRIPTION OF THE DRAWING

The accompanying photographic drawing illustrates the new cultivar, the color being a nearly true as possible with color illustrations of this type.

DESCRIPTION OF THE NEW PLANT

The following detailed description sets forth the characteristics of the new cultivar. The data which defines these characteristics were collected from asexual reproductions carried out by Oglevee, Ltd. in Connellsville, Pa. The color readings were determined under cool white light (200 F.C.) at 10:00 a.m. on Feb. 28, 1996 at Connellsville, Pa. Color references are primarily to The R.H.S. Colour Chart of The Royal Horticultural Society of London.

The plant:

*Form.*—Formal; bracts upright, not drooping.
*Height.*—350–37.0 cm.
*Spread.*—53.0–54.5 cm.
*Growth habit.*—Moderately compact.
*Branching.*—Self-branching.
*Rooting.*—Fast.
*Blooming habit.*—8 week response.
*Blooming season.*—Plant is saleable 6 weeks from initiation.

Foliage:

*Size.*—12.0–16.0 cm long, 8.5 cm–10.5 cm wide.
*Quantity.*—Average.
*Color.*—New foliage — Upper side, Green Group 139 A. Under side, Green Group 137 B. Old foliage — Upper side, Green Group 139 A. Under side, Green Group 137 B. Leaf petiole — Greyed-Purple Group 183 A.
*Shape.*—Ovate.
*Texture.*—Veins slightly pronounced; not reflective; "V" shaped; rippled.
*Edge of margin.*—Lobed.
*Borne.*—Slightly drooped; dark green foliage is readily visible beneath the bracts.
*Veins.*—Pattern — Pinnate.
*Color.*—Green Group 138 B; distinctive veins are lighter shade of green than body of leaf and mid-vein shows a hint of Greyed-Purple Group 183 A.
*Disease resistance.*—Considerable resistance to Botrytis.

Flower:

*Borne.*—Prominent on short stalks; held tightly together as a very visible cluster.
*Quantity.*—About 30% more cyathia on average (19-27 cyathia) than other varieties in this market class.
*Number of nectaries.*—One nectary per cyathium.
*Size.*—Average cyathia 8.0 mm long, 7.0 mm wide.

*Color.*—Green with Yellow Group 13B cyathia tipped with red.

Bracts:

*Size.*—Large; spread is 30–41 cm in diameter; individuals are 8–10 cm wide by 13–18 cm long.

*Borne.*—6–8 bracts per stem on a pinched plant grown in a 15 cm pot.

*Number of layers.*—Triple.

*Quantity.*—20 to 30 bracts.

*Shape.*—Primary bracts — Ovate. Secondary bracts — Obovate to elliptic.

*Color.*—Upper side — Red Group 45C. Lower side — Red Group 47B.

*Resistance to fade.*—Very strong resistance to color fade and greying; bract coloration remains bright and vibrant throughout blooming period; holds color up to 2 weeks later than current varieties.

*Margin.*—Primary bracts — Lobed with 1–2 indentations on each side. Secondary bracts — Entire.

*Vein location.*—Pinnate.

Reproductive organs: — Typical for poinsettia cultivars.

*Stamens.*—Number — 18 to 27. Color — White.

*Pollen color.*—Yellow.

*Ovary color.*—Green Group 138 B.

*Nectar cup color.*—Yellow Group 13 C with Red Group 45 C edges.

Shipping qualities: Very good postharvest qualities in both the greenhouse and the home.

I claim:

1. A new and distinct variety of poinsettia plant as herein shown and described, particularly characterized by its dark green foliage, intense rich red multilayered and nondrooping bracts having strong stems and a broad base, fully developed cyathia, early flowering, free branching and very long postharvest quality.

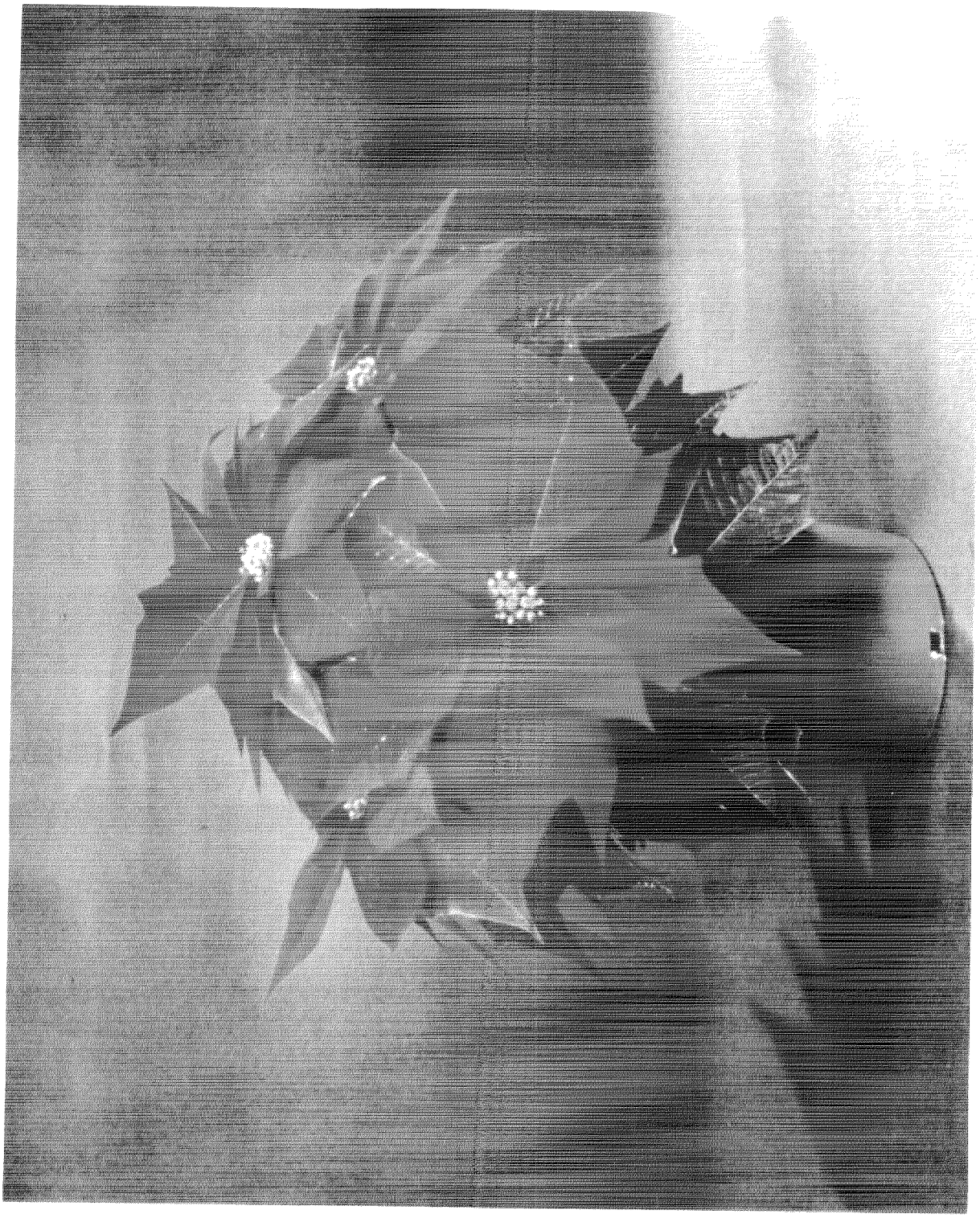

* * * * *